(12) United States Patent
Geiselhart

(10) Patent No.: US 8,939,968 B2
(45) Date of Patent: Jan. 27, 2015

(54) CRYOSURGICAL INSTRUMENT

(75) Inventor: Franz Geiselhart, Reutlingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 1193 days.

(21) Appl. No.: 12/918,587

(22) PCT Filed: Feb. 11, 2009

(86) PCT No.: PCT/EP2009/000956
§ 371 (c)(1),
(2), (4) Date: Sep. 27, 2010

(87) PCT Pub. No.: WO2009/103448
PCT Pub. Date: Aug. 27, 2009

(65) Prior Publication Data
US 2011/0022040 A1   Jan. 27, 2011

(30) Foreign Application Priority Data
Feb. 21, 2008   (DE) .......................... 10 2008 010 477

(51) Int. Cl.
*A61B 18/18*   (2006.01)
*A61B 18/02*   (2006.01)
*A61B 18/00*   (2006.01)

(52) U.S. Cl.
CPC ....... *A61B 18/02* (2013.01); *A61B 2018/00017* (2013.01); *A61B 2018/00023* (2013.01); *F25B 2309/021* (2013.01)
USPC ............................................. 606/23; 606/20

(58) Field of Classification Search
USPC ..................................................... 606/20–26
See application file for complete search history.

(56) References Cited

U.S. PATENT DOCUMENTS

| | | |
|---|---|---|
| 3,613,689 A | 10/1971 | Crump et al. |
| 5,254,116 A | 10/1993 | Baust et al. |
| 6,270,493 B1 | 8/2001 | Lalonde et al. |
| 6,942,659 B2 | 9/2005 | Lehmann et al. |
| 2003/0023288 A1 | 1/2003 | Magers |
| 2004/0054361 A1 | 3/2004 | Lehmann et al. |

FOREIGN PATENT DOCUMENTS

| | | |
|---|---|---|
| EP | 0 007 103 B1 | 1/1980 |
| WO | WO 99/04211 A1 | 1/1999 |
| WO | WO 2005/000106 A2 | 1/2005 |

OTHER PUBLICATIONS

Written Opinion from PCT/EP/2009/000956.

*Primary Examiner* — Linda Dvorak
*Assistant Examiner* — Amanda Scott
(74) *Attorney, Agent, or Firm* — Dickstein Shapiro LLP

(57) ABSTRACT

A cryosurgical instrument, comprising a cryoprobe having ducting through which a compressed cooling fluid, such as a cooling gas, flows, for cooling a least part of the cryoprobe. The ducting has an expansion channel having a channel cross-section that enlarges progressively in the flow, direction over a predetermined length such that the compressed cooling gas gradually decompresses, at least partially, beyond a predetermined length on its flow path through the expansion channel while simultaneously cooling down.

18 Claims, 4 Drawing Sheets

CRYOSURGICAL INSTRUMENT

FIELD OF THE INVENTION

Embodiments disclosed herein relate to a cryosurgical instrument comprising a cryoprobe having ducting through which a compressed cooling fluid, such as a cooling gas, flows for cooling a least part of the cryoprobe.

BACKGROUND

Targeted, controlled use of cold material is used in cryosurgery to devitalize biological tissue. In addition, particularly using flexible probes, foreign bodies are extracted from body cavities by freezing them solid on the cryoprobe or on a probe head; these foreign bodies include for example, swallowed and at the same time accidentally inhaled foreign bodies that must be removed from the respiratory tract. Cryosurgery is, however, also suitable for obtaining tissue samples (biopsy). In this case, a specific area of tissue, the tissue sample, freezes onto the probe head and after separation from the surrounding tissue can be made accessible for examination.

There are various possibilities for deep freezing in surgery. One is based on the Joule-Thomson effect: the atoms or molecules of an expanding fluid and in particular of a gas below the inversion temperature work against mutual attraction with the result that the gas loses internal energy. It cools down. Usually $CO_2$ or $N_2O$ are used as the expanding fluid or gas—referred to below as cooling fluid or cooling gas.

Cryosurgical instruments of the type just described usually have a probe that can be transported to the tissue to be treated and also gas line devices which penetrate the probes and release the working gas into the inner volume of the probes where it expands and results cooling down the probe. Since these probes are preferably made of thermally conductive material, this ensures elimination of the tissue heat via the probe and therefore a cooling effect.

In cryoprobes where the cooling effect is generated by decompressing compressed gases, there is frequently a requirement for cooling a larger surface evenly or in accordance with a specific temperature profile. For example, a cryoprobe with a 2 mm diameter is supposed to be cooled evenly over a length of 50 mm.

In such cases, according to the prior art, a plurality of nozzles are distributed inside the cryoprobe to achieve reasonably even cooling. The larger the number of cooling nozzles used, the more evenly the resulting temperature is reached over the length selected. With this procedure, the amount of gas required is divided between a plurality of nozzles. Consequently, the individual nozzles are very small in diameter. At the same time, however, production is disproportionately time-consuming. With small nozzles, close tolerances are placed on the geometry to achieve a constant flow behavior. On principle, smaller nozzle cross-sections are also more susceptible to blockages.

It has also turned out that with cryosurgical instruments according to the prior art it is difficult to implement an essentially constant temperature curve or a predetermined temperature curve. Moreover, the construction of the prior art cryoprobes is very time-consuming and cost-intensive.

SUMMARY

Consequently, the object of the embodiments disclosed herein is to develop a cryosurgical instrument of the type referred to above in such a manner that it is possible to achieve more even cooling of the cryoprobe that is technically easier to implement.

In particular, this object is achieved by a cryosurgical instrument comprising a cryoprobe having ducting through which a compressed cooling fluid such as a cooling gas flows for cooling a least part of the cryoprobe. The ducting has an expansion channel having a channel cross-section that enlarges progressively in the flow direction over a predetermined length such that the compressed cooling gas gradually decompresses, at least partially, beyond a predetermined length on its flow path through the expansion channel while simultaneously cooling down.

An aspect of the embodiments is to design a channel running over a predetermined length such that its cross-section over this length increases in such a way that expansion of the gas is distributed over this length. As a result, at the beginning of the channel there is only partial expansion and therefore not a full temperature difference. However, due to progressive expansion over the entire length, cooling occurs over a large area wherein the temperature achieved on the outside of the probe or the distribution thereof depends, among other things, on the widening of the cross-section in each case and the heat transfer resistance between the expansion channel and the outside of the cryoprobe.

Preferably, in this case, the expansion channel is in a thermally conductive relationship with the outside of the cryoprobe via a heat conductor. Either independent components with a reduced heat transfer resistance or appropriate auxiliary means, such as thermal compounds, etc. may be used as heat conductors. It should be appreciated that beyond this, it is also possible to design a housing component of the cryoprobe as a heat conductor and to construct it of a material that guarantees optimum heat transfer. The expansion channel is preferably disposed as close as possible to the outside of the cryoprobe or close to the areas that are supposed to be cooled.

In at least one embodiment, the expansion channel has a channel cross-section designed as a function of a heat transfer resistance of the heat conductor such that on the outside of the cryoprobe a predetermined temperature distribution, and in particular a constant temperature, adjusts itself at least over a section defined by the predetermined length discusses above. This means that, for example, in very thick wall sections between the expansion channel and the outside or the region to be cooled, the expansion channel is correspondingly designed to be significantly widened to achieve particularly effective expansion and cooling at this point. It should be appreciated that it is also possible to make appropriate adaptations to the expansion channel in regions on the outside of the cryoprobe where extreme cooling is desired. With a specific adaptation of the expansion channel's cross-section, it is thus possible to achieve an even or any other desirable temperature distribution on the outside of the cryoprobe, considering, for example, the existing wall thicknesses to the outside, the flow velocity, etc.

The expansion channel is preferably formed such that the cooling gas flows in a turbulent flow. Of course, significant here, among other things, are the flow resistance in the expansion channel, the expansion channel cross-section and also the cooling fluid pressure, which is provided by an external cooling fluid supply. The advantage of the turbulent flow in the expansion channel is that it results in very effective heat dissipation and improved cooling of the outside of the cryoprobe.

Preferably, for the formation of the expansion channel, at least one modeling component that in particular tapers/widens in the flow direction is disposed in at least one section of the line system such that the resulting channel cross-section progressively enlarges in the flow direction. If the ducting is a channel limited by side walls, then the modeling component may be disposed on at least one of these side walls as a component such as e.g., a wedge-shaped component tapering in the flow direction, resulting in just such a widening expansion channel through which the cooling fluid can flow with simultaneous progressive decompression and cooling. In place of the tapering, i.e., the wedge-shaped component, it is also possible to use a modeling component in the form of a hollow body such as for example, a component with an essentially central hole, the wall of said hole widening progressively in the flow direction which likewise leads to a widening expansion channel.

Preferably, the expansion channel is formed by a tube and a modeling component that is inserted into the tube as a frusto-conical or similarly rotationally symmetrical, tapering component. Depending on the desired temperature distribution on the outside of the cryoprobe, it is also possible to change the shape of the modeling component and thus have a direct influence on the cooling effect. In this context, it is also possible to insert into the tube a modeling component in the form of a hollow body, the hollow body walls are designed to progressively widen in the flow direction such that the result is also a widening expansion channel. This corresponds substantially to the geometry referred to above of the widening hollow body component disposed in the channel and in particular a rotationally symmetrical hollow body as a modeling component.

The tube forms, at least in part, a cryoprobe housing wherein the tube preferably consists of a material that has good thermal conductivity. Such an embodiment of the cryoprobe enables very easy and cost-effective production of the cryoprobe in accordance with the configurations referred to above.

It should be appreciated that it is possible to use other modeling components or modeling component assemblies instead of the tapering or widening modeling components referred to above to create a cross-section of the ducting that enlarges progressively in the flow direction and thus an expansion channel for cooling the outside of the cryoprobe.

In an embodiment, the tube preferably has an internal thread and the modeling component has a complementary external thread on a tapering wall with which it can be screwed into the tube forming an expansion channel in the resulting thread pitch that enlarges progressively in the flow direction. Because the expansion channel runs substantially in the form of a helix around the modeling component, the expansion path enlarges and thus the maximum cooling capacity to be achieved increases. Moreover, such an embodiment enables much more comprehensive cooling of the cryoprobe. It should also be appreciated that with an appropriate choice of different thread types it is also possible to influence the resulting outer temperature and its distribution.

In an embodiment, the tube has an internal thread and the modeling component has a complementary external thread with which it can be screwed into the tube forming the expansion channel in the resulting thread pitch, wherein the external thread is formed as a conical or similar thread running in the flow direction and/or the internal thread is formed as a conical or similar thread running in the opposite direction. A conical thread here is understood to be a thread or threads where the thread pitch depth increases progressively similar to the external geometry of a cone. On screwing into a complementary external or internal thread this produces an expansion channel with a cross-section that expands in the flow direction.

It should be appreciated that it is also possible to form comparable channels, grooves, etc. in the tube or modeling component in place of any type of thread described above to create a corresponding expansion channel. In this case, all methods known in the art may be used for the creation of flow channels.

The expansion channel is preferably formed between an outer tube and an inner tube running therein. The result of this is that the warmer cooling fluid can be fed in through the inner tube to expand in the expansion channel located further to the outside and to cool the outside of the outer tube effectively. In connection with this, the outer tube may be used as a cryoprobe housing or may be joined to such a housing by way of an appropriate heat conductor.

All of the embodiments discussed above may be used to form the progressively widening expansion channel in the double-walled tube, whereby the modeling component is then insertable in the outer channel or integrated therein. It is also possible to use a hollow body component as the modeling component whereby its hollow body region functions as a centrally disposed intake.

The cryoprobe preferably comprises a cryoprobe tip that is disposed at one tube end of the double-walled tube and that brings the inner tube into fluid communication with the expansion channel forming a deflecting channel. In this way, the inner tube and the outer tube or the external channel formed in the outer tube may be used to feed in and discharge the cooling fluid, i.e., the cooling gas. The resulting geometric outer shape of such a tube corresponds to a cannula and thus to a shape that is very user-friendly for cryosurgery.

The cryoprobe tip is preferably disposed on the tube end and is capable of being screwed on and off by way of a threaded device such that the cross-section of the deflecting channel is variable and is adaptable to an inlet region of the expansion channel. One advantage is that by adapting the deflecting channel it is also possible to influence a possible expansion of the cooling fluid gas in the cryoprobe's tip region.

Preferably disposed around the inner tube of a double-walled tube and running helically with increasing pitch in the flow direction, is a modeling component, such as a wire, which is in fluid-tight connection with the walls of both tubes respectively such that a helical expansion channel, increasing progressively in cross-section, is formed between adjacent turns and the walls. It is also possible to influence the geometry and the cross-section of the expansion channel by the choice of the circumferential modeling component used. Thus, it is possible for example, to produce a progressively widening expansion channel by using a progressively tapering modeling component that is applied to the inner tube with an even helical pitch.

Basically, the modeling component has good thermal conductivity, particularly in the region facing outwards, to ensure effective cooling of the outside or the regions of the cryoprobe to be cooled. To achieve effective cooling of the outside, it is also possible to arrange appropriate insulating layers in the region facing inwards; that is, for example, the region adjoining the intake with the "warm" cooling fluid prior to its decompression. This can be achieved by the use of appropriate intermediate insulating layers or by an appropriate choice of material for the modeling component or for the inner tube, etc.

Basically, it is possible to wind the helical modeling component onto the inner tube, or to introduce it in the shape of an independent helix into the intermediate space between inner tube and outer tube and in particular to screw it in.

In an embodiment, the modeling component is formed integrally on the inner tube and/or on the outer tube and in particular by means of a helical groove in the relevant walls of the tube wherein the pitch of the helical groove and/or its width increases in the flow direction. Thus, an expansion channel, which runs helically around the inner tube and is widened in cross-section in such a manner that there is progressive decompression of the gas and thus cooling over the entire length of the expansion channel, can also be created in this way. It is also possible to create comparatively colder and less cold regions, if this is necessary, by appropriately altering the cross-section over the length of the expansion channel. It is also possible to create the modeling components formed integrally on the inner tube and/or on the outer tube by means of cutouts of the adjacent areas, which then fit precisely on the complementary tube wall. It is also possible to arrange corresponding guide grooves or devices on one or both tubes, which enable the insertion of a helical modeling component. It is also possible to provide a plurality of different grooves in order, for example, to insert different modeling components or to achieve different pitches, cross-section changes, etc.

In connection with modeling components that are insertable in the ducting and in the outer channel of a double-walled tube, it is also conceivable to design the modeling component flexibly such that the expansion channel can be modified as required. Thus, for example, by inserting a resilient helix that fits accurately over the inner tube and has a thread rising in the flow direction, the thread also being present in a perfect fit on the wall of the outer tube, it is possible to influence the change in the expansion channel's cross-section by moving or turning the helix in the axial direction of the tube.

It should be appreciated that an adaptation may also be carried out using multi-part modeling components that permit a change in the expansion channel's cross-section over its length.

This adaptation is preferably possible by way of a handle on the cryoprobe device or via an external control device so that the cryoprobe's temperature can also be controlled during the operation. In this case, all methods for the control of a surgical instrument known in the art may be used.

BRIEF DESCRIPTION OF THE DRAWINGS

Embodiments of the invention will be described in greater detail with reference to the associated drawings, in which.

DETAILED DESCRIPTION

Figure 1:
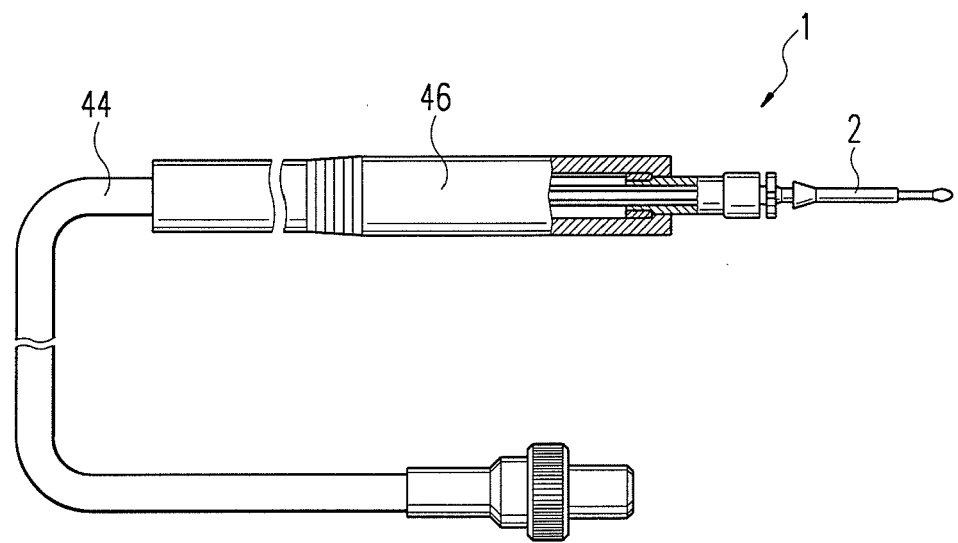
FIG. 1 illustrates a schematic diagram of a cryosurgical device according to an embodiment disclosed herein.

Throughout the description, the same reference numerals are to refer to identical parts and parts acting in an identical manner.

FIG. 1 shows an isometric drawing of an embodiment of a cryosurgical instrument 1 disclosed herein. Instrument 1 comprises a cryoprobe holder 46 and a cryoprobe 2 insertable therein, which is coolable according to the embodiments disclosed herein by ducting, the design of which is described in greater detail below, in such a manner that it can be used to perform cryosurgical operations.

The cryosurgical instrument 1 is equipped with gas supply line fittings 44, which enable connection to a gas reservoir (not illustrated) or a similar gas supply.

Figure 2:
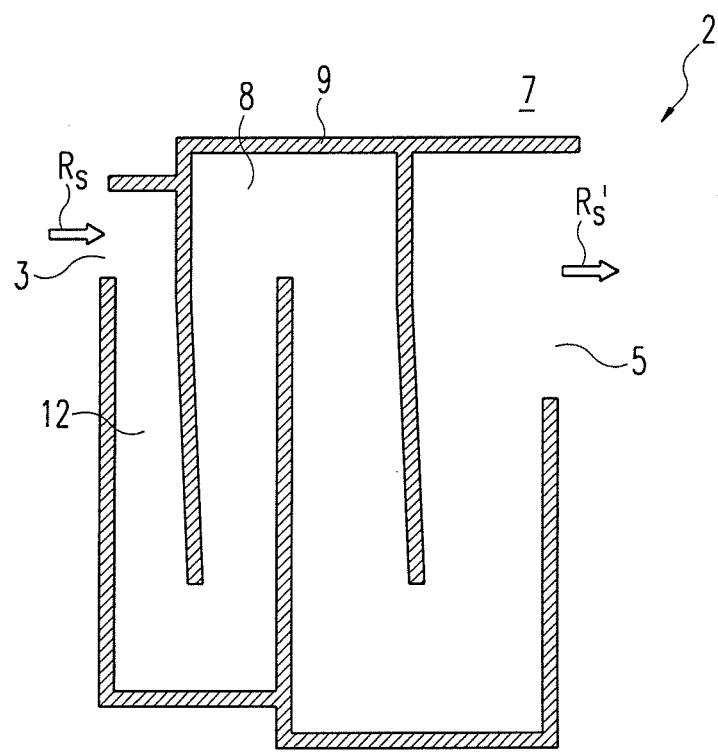
FIG. 2 illustrates a first embodiment of a cryoprobe of the cryosurgical device in FIG. 1.
Figure 3:
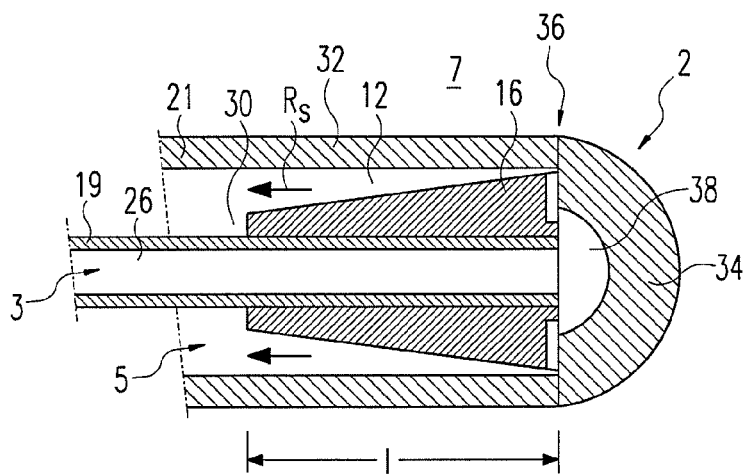
FIG. 3 is a second embodiment of a cryoprobe of the cryosurgical device in FIG. 1.

FIG. 2 shows a schematic diagram of a first embodiment of cryoprobe 2. The embodiment is designed substantially with a cryoprobe surface that has substantially two-dimensional, meandering ducting 8 through which a cooling gas flows in a flow direction $R_S$.

In this embodiment, ducting 8 is designed such that it has a cross-section that widens over the flow path along flow direction $R_S$, forming an expansion channel 12. Consequently, the cooling gas flowing through intake 3 decompresses progressively on its way through expansion channel 12 to a discharge 5 and thus cools down according to the Joule-Thomson effect. Thus, an outside 7 of cryoprobe 2 can effectively be cooled by the correspondingly thermally conductive design of channel walls 9 of ducting 8.

FIGS. 3-9 illustrate further embodiments of cryoprobe 2 according to the embodiments described herein wherein the probes are basically formed from a double-walled tube comprising an inner tube 19 and an outer tube 21. In this case, inner tube 19 acts as intake 3 through which the cooling fluid can be routed through the cryoprobe 2. Disposed on free end 36 is a cryoprobe tip 34, which forms a deflecting channel 38 thus establishing a connection between inner channel 26 of inner tube 19 and outer channel 30, said channel being formed by inner tube 19 and outer tube 21.

Disposed in this outer channel 30 is a modeling component 16, which tapers in flow direction $R_S$ such that an expansion channel 12 that tapers progressively over a length 1 is formed. Cooling fluid, which flows via intake 3 through channel 26 and then into expansion channel 12 (via deflecting channel 38), expands therein progressively over length 1 such that it cools down and cooling occurs on outside 7 of cooling probe 2 by way of the thermally conductive outer wall 32 of outer channel 30.

Since the illustrated cryoprobe 2 is formed to be rotationally symmetrical from a double-walled tube with a constantly thick outer wall 32 and from a correspondingly rotationally symmetrical, tapering hollow body as modeling component 16, there is also even cooling over the circumference of cryoprobe 2. It is also possible to achieve uneven cooling over the circumference of cryoprobe 2 by an appropriately modified version of modeling component 16 or the position of inner tube 19 in relation to outer tube 21.

Figure 4:
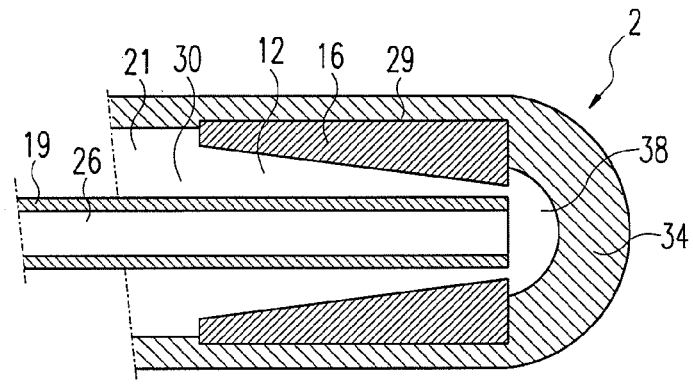
FIG. 4 illustrates a third embodiment of a cryoprobe of the cryosurgical device in FIG. 1.

FIG. 4 illustrates a third embodiment of cryoprobe 2, again comprising an inner tube 19 and an outer tube 21, of which channels 26 and 30, respectively, are in fluid communication with each other by a cryoprobe tip 34 and a deflecting channel 38 resulting therefrom. In this embodiment, a modeling component 16 is also inserted in outer channel 30 to form an expansion channel 12. Here, modeling component 16 is designed as a rotationally symmetrical hollow cylinder with progressively widening inner walls. In order to fix hollow cylinder 16 in its position within outer tube 21, the tube has insertion grooves 29 that enable custom-fit insertion.

Figure 5:
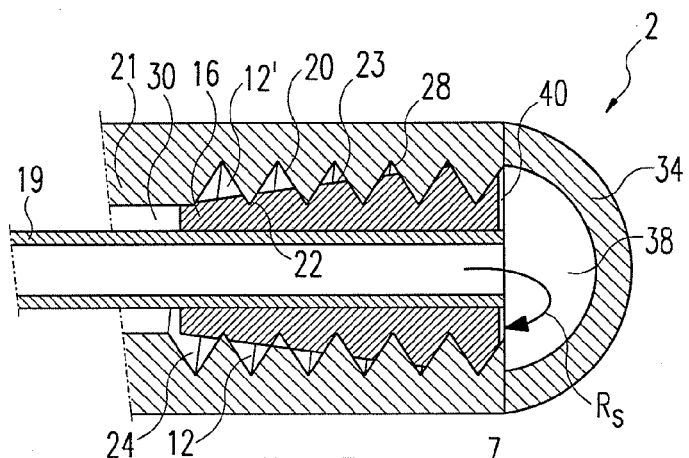
FIG. 5 illustrates a fourth embodiment of a cryoprobe of the cryosurgical device in FIG. 1.

FIG. 5 illustrates a fourth embodiment of cryoprobe tip 2, which also comprises a double-walled tube 19, 21 in the outer channel 30 of which a modeling component 16 is inserted to form expansion channel 12.

Unlike the embodiments described above, the illustrated modeling component 16 comprises an external thread 22 on a tapering wall 23. The thread is capable of being screwed into an internal thread 20 formed on inner wall 28 of outer tube 21.

Due to the design of external thread 22 on inclined or tapering wall 23, when this component is screwed into internal thread 20 on outer tube 21 a progressively widening thread pitch 24 is produced, which acts as expansion channel 12. This channel is in fluid communication at an inlet region 40 with a deflecting channel 38 being formed by a cryoprobe tip 34 such that cooling fluid, expanding in flow direction $R_S$, can flow via inner tube 19 through expansion channel 12 extending circumferentially in the form of a helix to cool down outside 7 of cryoprobe 2.

It is also possible to additionally influence the cooling effect on outside 7 with an appropriate choice of thread pitch and the depth of relevant thread pitch 24.

Figure 6:
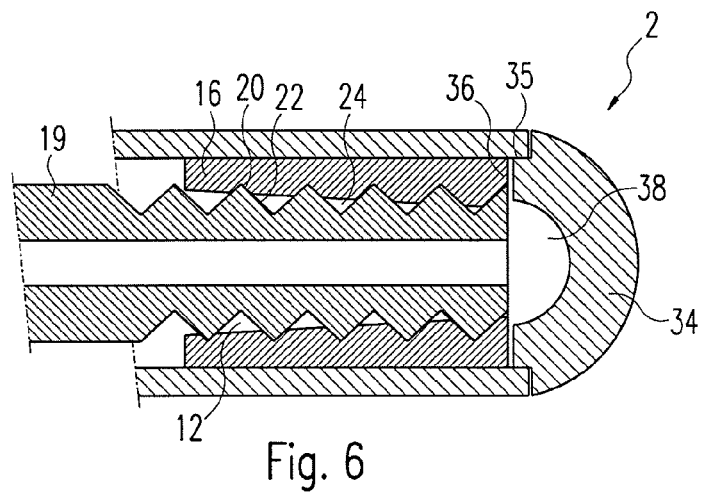
FIG. 6 illustrates a fifth embodiment of a cryoprobe of the cryosurgical device in FIG. 1.

FIG. 6 illustrates a fifth embodiment of cryoprobe 2. Unlike previous embodiments, modeling component 16 is designed as a widening hollow cylinder having an internal thread 20 that is complementary to an external thread 22 of inner tube 18 in such a manner that modeling component 16 can be screwed onto tube 19 forming a circumferential expansion channel 12 in the form of a helix in thread pitch 24 of the two complementary threads 20, 22.

Moreover, in this embodiment, cryoprobe 2 comprises a cryoprobe tip 34 that can be screwed via a threaded region 35 onto a free end 36 of double-walled tube 19, 21 in such a manner that the size of deflecting channel 38 formed by cryoprobe tip 34 is adaptable by screwing cryoprobe tip 34 in or out.

Figure 7:
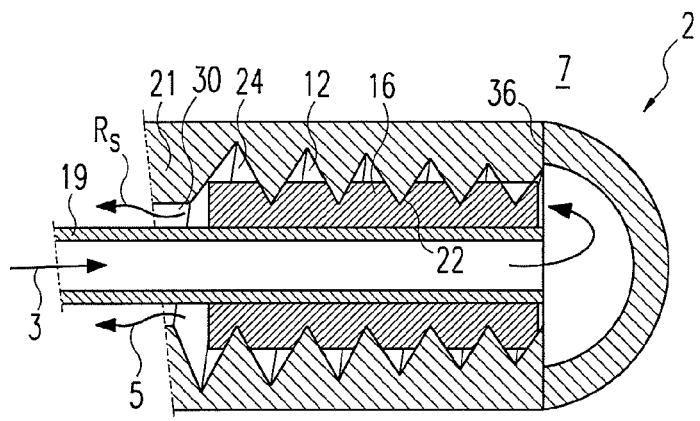
FIG. 7 illustrates a sixth embodiment of a cryoprobe of the cryosurgical device in FIG. 1.

FIG. 7 shows a sixth embodiment of cryoprobe 2, which also comprises a double-walled tube 19, 21, wherein inner tube 19 acts as intake 3 and outer tube 21 or outer channel 30 formed between inner tube 19 and outer tube 21 acts as return 5.

A modeling component 16 that has an external thread 22 is inserted in outer channel 30 to form an expansion channel 12. Tube 21 has a complementary internal thread 20 for this purpose, said thread being designed as a conical thread running contrary to flow direction $R_S$. This means that the cross-section of thread pitch 24 and expansion channel 12 enlarges progressively in the flow direction due to this conical thread running contrary to the flow direction and thus, as in the embodiments described above, widens progressively. It should be appreciated that it would also be possible to design an increasing thread pitch instead of the even thread pitch or to taper modeling component 16 correspondingly to achieve e.g., cooling of outside 7 that becomes more intense towards free end 36 of cryoprobe 2.

Alternatively, or in addition to, it is also possible to arrange a conical thread 22 running in the flow direction in modeling component 16 instead of thread 20, running contrary to flow direction $R_S$, in outer tube 21.

Figure 8:
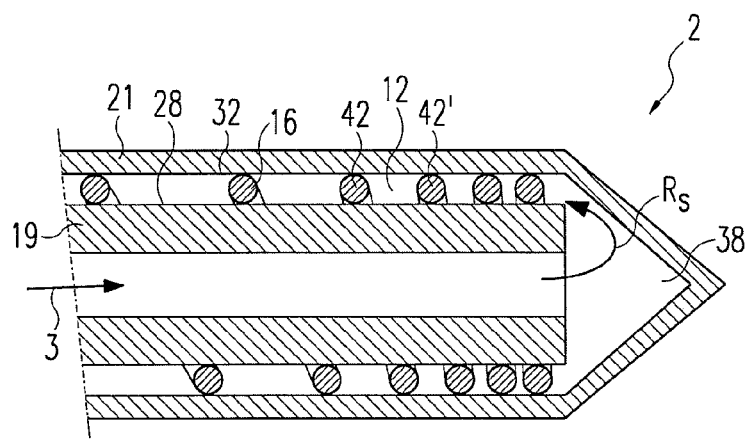
FIG. 8 illustrates a seventh embodiment of a cryoprobe of the cryosurgical device in FIG. 1.

FIG. 8 shows a seventh embodiment of cryoprobe 2, in which a modeling component 16, in this case a wire, running around inner tube 19 in the form of a helix is wound between an inner tube 19 acting as intake 3 and an outer tube 21 on both walls 28, 32 of tubes 19, 21 such that between individual turns 42, 42' and respective walls 28, 32 an expansion channel 12 is formed that also runs around inner tube 19 in the form of a helix that widens progressively. A cooling fluid entering in direction of flow $R_S$ via inner tube 19 or intake 3 flows back via a circulation channel 38 into this helical expansion channel 12 where it gradually expands and cools down due to the progressively enlarging cross-section. Modeling component 16 or the wire may in this case be both an independent component wound onto inner tube 19 and may also be a component integral therewith and/or with outer tube 21. In addition, it is also possible to guide modeling component 16 in corresponding grooves or similar guidance devices (not illustrated) to make positioning it easier.

Figure 9:
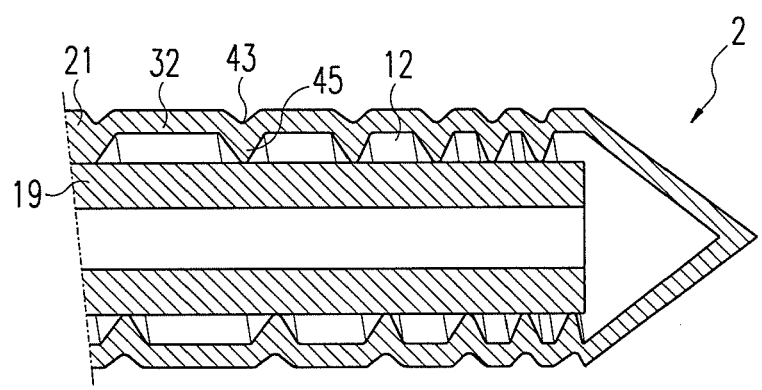
FIG. 9 illustrates an eighth embodiment of a cryoprobe of the cryosurgical device in FIG. 1.

FIG. 9 shows an eighth embodiment of cryoprobe 2, which functions according to the same principle as the embodiment of FIG. 8. Instead of modeling component 16 being executed as a wire, in the illustrated embodiment, an appropriate groove 43 is disposed on outer wall 32 of outer tube 21 in such a manner that resulting protrusion 45 presses fluid-tight on inner tube 19. As groove 43 is applied to outer tube 21 helically and with increasing pitch, a circumferential, progressively widening expansion channel 12 arises between the individual turns of groove 43 or protrusion 45, which channel the gas flows along and decompresses as it gradually cools down.

Figure 10:
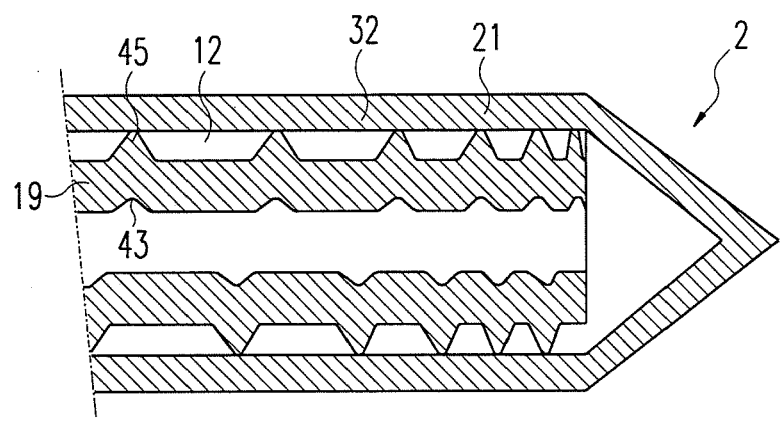
FIG. 10 illustrates a further embodiment of a cryoprobe disclosed herein.

FIG. 10 shows a similar embodiment in which grooves 43 or protrusions 45 are disposed on inner tube 19 such that protrusions 45 are in fluid-tight contact with outer tube 21 or its wall 32 while forming a corresponding expansion channel 12.

It should be noted that in addition to the embodiments of the modeling component illustrated herein, all modeling components that enable the formation of an expansion channel that enlarges progressively in cross-section may be used. It is also conceivable to execute the tube or outer tube 21 as a conically widening tube, etc.

In connection with circumferential thread pitches for forming the expansion channel, it is also possible to use double and multiple helixes or similarly several in particular concentrically winding pitches or channels, etc.

The invention claimed is:

1. A cryosurgical instrument, comprising:
    a cryoprobe, having a housing and ducting through which a compressed cooling fluid flows for cooling at least part of the cryoprobe,
    wherein the ducting has an expansion channel having a channel cross-section that enlarges progressively in the flow direction over a predetermined length such that the compressed cooling fluid gradually decompresses, at least partially, beyond a predetermined length on its flow path through the expansion channel while simultaneously cooling down,
    wherein the expansion channel is formed between an outer tube and an inner tube running within the outer tube, and
    wherein the outer tube is part of the housing of the cyroprobe or thermally connected thereto.

2. The cryosurgical instrument of claim 1, wherein:
    the expansion channel is in a thermally conductive relationship with an outside of the cryoprobe via a heat conductor.

3. The cryosurgical instrument of claim 2, wherein:
    the expansion channel has a channel cross-section designed as a function of a heat transfer resistance of the heat conductor such that on the outside of the cryoprobe a predetermined temperature distribution adjusts itself at least over a section defined by the predetermined length.

4. The cryosurgical instrument of claim 3, wherein the predetermined temperature distribution is a constant temperature.

5. The cryosurgical instrument of claim 1, wherein:
the expansion channel is formed such that the cooling fluid flows in a turbulent flow.

6. The cryosurgical instrument of claim 1, wherein:
for the formation of the expansion channel, at least one modeling component that tapers/widens in the flow direction is disposed in at least one section of the ducting such that the resulting channel cross-section progressively enlarges in the flow direction.

7. The cryosurgical instrument of claim 6, wherein:
the expansion channel is formed by a tube and a modeling component that is inserted into the tube as a rotationally symmetrical hollow-body component that widens in the flow direction.

8. The cryosurgical instrument of claim 6, wherein:
the expansion channel is formed by a tube and a modeling component that is inserted into the tube as a frusto-conical or similarly rotationally symmetrical component tapering in the flow direction.

9. The cryosurgical instrument of claim 8, wherein:
the tube at least partially forms a cryoprobe housing of the cryoprobe.

10. The cryosurgical instrument of claim 8, wherein:
the tube has an internal thread and the modeling component has a complementary external thread on a tapering wall with which it can be screwed into the tube forming an expansion channel in the resulting thread pitch that enlarges progressively in the flow direction.

11. The cryosurgical instrument of claim 8, wherein:
the tube has an internal thread and the modeling component has a complementary external thread with which it can be screwed into the tube forming the expansion channel in the resulting thread pitch, wherein the external thread is formed as a conical or similar thread running in the flow direction and/or the internal thread is formed as a conical or similar thread running in the opposite direction.

12. The cryosurgical instrument of claim 8, further comprising:
a cryoprobe tip that is disposed at one tube end and that brings the inner tube into fluid communication with the expansion channel forming a deflecting channel.

13. The cryosurgical instrument of claim 12, wherein:
the cryoprobe tip is disposed on the tube end and is capable of being screwed on and off by way of a threaded device such that the cross-section of the deflecting channel is variable and is adaptable to an inlet region of the expansion channel.

14. The cryosurgical instrument of claim 8, wherein:
the inner tube has an external thread and the modeling component is formed as a rotationally symmetrical hollow body widening progressively in the flow direction, said hollow body having on its inner hollow-body wall an internal thread and which using this is screwed onto the external thread of the inner tube forming the expansion channel in the thread pitch.

15. The cryosurgical instrument of claim 8, wherein:
disposed around the inner tube running in the form of a helix, with increasing pitch in the flow direction, is a modeling component wire, which is in fluid-tight connection with the walls of both tubes respectively such that a helical expansion channel increasing progressively in cross-section is formed between adjacent turns and the walls.

16. The cryosurgical instrument of claim 15, wherein:
the modeling component wire is formed integrally on the inner tube and/or on the outer tube by a helical groove of the relevant wall of the tube, and the pitch of the helical groove and/or its width increases in the flow direction.

17. The cryosurgical instrument of claim 1, wherein the cooling fluid is a cooling gas.

18. A cryoprobe comprising:
a housing and ducting through which a compressed cooling gas flows for cooling at least part of the cryoprobe, wherein the ducting has an expansion channel having a channel cross-section that enlarges progressively in the flow direction over a predetermined length such that the compressed cooling gas gradually decompresses, at least partially, beyond a predetermined length on its flow path through the expansion channel while simultaneously cooling down, wherein the expansion channel is formed between an outer tube and an inner tube running within the outer tube, and wherein the outer tube is part of the housing or thermally connected thereto.

* * * * *